(12) United States Patent
Kross

(10) Patent No.: US 9,295,681 B2
(45) Date of Patent: *Mar. 29, 2016

(54) MULTIFUNCTIONAL TOPICAL FORMULATION FOR THE TREATMENT OF ACNE VULGARIS AND OTHER SKIN CONDITIONS

(71) Applicant: Kantian Sciences Corporation, Smithtown, NY (US)

(72) Inventor: Robert D. Kross, Bellmore, NY (US)

(73) Assignee: Kantian Sciences Corporation, Smithtown, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/564,201

(22) Filed: Dec. 9, 2014

(65) Prior Publication Data

US 2015/0094286 A1    Apr. 2, 2015

Related U.S. Application Data

(60) Continuation of application No. 13/762,829, filed on Feb. 8, 2013, now Pat. No. 8,932,650, which is a division of application No. 13/345,839, filed on Jan. 9, 2012, now abandoned.

(60) Provisional application No. 61/460,940, filed on Jan. 11, 2011.

(51) Int. Cl.
| | |
|---|---|
| *A61K 33/00* | (2006.01) |
| *A61K 31/60* | (2006.01) |
| *A61K 31/192* | (2006.01) |
| *A61K 31/19* | (2006.01) |
| *A61K 31/194* | (2006.01) |
| *A61K 9/00* | (2006.01) |
| *A61K 9/08* | (2006.01) |
| *A61K 47/38* | (2006.01) |

(52) U.S. Cl.
CPC ............. *A61K 31/60* (2013.01); *A61K 9/0014* (2013.01); *A61K 9/08* (2013.01); *A61K 31/19* (2013.01); *A61K 31/192* (2013.01); *A61K 31/194* (2013.01); *A61K 33/00* (2013.01); *A61K 47/38* (2013.01)

(58) Field of Classification Search
None
See application file for complete search history.

(56) References Cited

U.S. PATENT DOCUMENTS

2003/0175362 A1* 9/2003 Kross et al. ............... 424/718
2004/0214891 A1* 10/2004 Marcinkiewicz et al. .... 514/553

* cited by examiner

*Primary Examiner* — Robert T Crow
*Assistant Examiner* — John P Nguyen
(74) *Attorney, Agent, or Firm* — Edwin D. Schindler

(57) ABSTRACT

A two-part aqueous composition for treating skin ailments, such as acne vulgaris, includes an acidic part having salicylic acid and an α-hydroxy acid, and an alkaline part having an alkaline nitrite salt. The α-hydroxy acid is preferably glycolic acid, lactic acid, malic acid, mandelic acid or a combination thereof. The alkaline nitrite salt is preferably sodium nitrite. The acidic part and the alkaline part are an acidic aqueous solution and an alkaline aqueous solution, respectively, which may either be mixed with one another then applied to an affected portion of a patient's skin or, alternatively, may be sequentially applied to the affected portion of the patient's skin, preferably within 15 minutes of one another.

7 Claims, No Drawings

MULTIFUNCTIONAL TOPICAL FORMULATION FOR THE TREATMENT OF ACNE VULGARIS AND OTHER SKIN CONDITIONS

CROSS-REFERENCE TO RELATED APPLICATIONS

This is a continuation of U.S. patent application Ser. No. 13/762,829, filed Feb. 8, 2013, now U.S. Pat. No. 8,932,650, which is a division of U.S. patent application Ser. No. 13/345,839, filed Jan. 9, 2012, now abandoned.

The inventor claims domestic priority, pursuant to 35 U.S.C. §119(e), on the basis of U.S. Provisional Patent Application Ser. No. 61/460,940, filed Jan. 11, 2011, the entire disclosure of which shall be deemed to be incorporated by reference herein.

BACKGROUND OF THE INVENTION

1. Technical Field of the Invention

The present invention relates, generally, to an aqueous composition with an enhanced efficacy in the treatment of acne vulgaris (i.e., common acne) and other skin conditions.

More particularly, the present invention relates to a multifunctional two-part liquid formulation that, upon combination of both phases, either initially ex-vivo or on the skin after sequential application of the two parts, creates a mixture of at least three beneficial acidic substances. These compositions are a complex of various powerful antimicrobial and keratolytic agents, where several of the acid substances serve more than one of these functions.

More specifically, the two-part liquid may be applied sequentially to the subject's skin with either part first applied, or the topical formulation may be applied to the subject's skin after the two parts have been combined. Each of the three alternate methods of application has certain advantages.

2. Description of the Prior Art

The inventive method and composition are directed to the treatment of a number of topical afflictions that heretofore have not been treatable by a multi-functional formulation and often not effectively treatable by any medication or other means. The areas in which this technology can find application includes the broad range of topical skin infections and disinfection, as well as conditions which involve both pathogenic microorganisms and physiologic dysfunction, and often a combination of both. In the latter category is the affliction termed acne, technically acne vulgaris, or common acne.

Acne is a common skin disease that is characterized by areas of skin with seborrhea (scaly red skin), comedones (blackheads and whiteheads), papules (pinheads), pustules (pimples), nodules (large papules) and often scarring. Acne affects mostly skin with the densest population of sebaceous follicles; these areas include the face, the upper part of the chest, and the back. In most cases, acne is an inflammatory condition, but it can also be manifest in non-inflammatory forms. The lesions are caused by hormonal stimulation of the skin's pilosebaceous units, skin structures consisting of hair follicles and their associated sebaceous glands. Increased activity of those gland results in an enhanced secretion of an oily/waxy matter, called sebum, which ordinarily functions to lubricate the skin and hair. Although the primary cause of acne is hyperactivity of the sebaceous gland, it is well recognized that a specific gram-positive microorganism, *Propionibacterium acnes*, is invariably found in large numbers on the skin of acne sufferers. It lives on the fatty acids in sebum, so the greater the amount of sebum, the greater the quantities of the organism that will be found. It is known that this anaerobic (aerotolerant) bacterium generates enzymes that degrade skin, and also creates proteins that may activate the immune system.

The topical treatment of acne generally involves a material directed to the control of the inflammatory aspect of the condition or the characteristic microorganism (*P. acnes*) that is present on the skin at levels in excess of normal as a result of the excess sebum "feedstock." A long-popular component of many topical acne medications is the $R_x$ ingredient benzoyl peroxide. Major factors contributing to its efficacy is its skin-irritating capacity and its capacity to help rid the follicles of excess dead skin cells. This lessens the chance of pore blockage. It has also been theorized to introduce oxygen into the pore, which is anathema to the anaerobic *P. acnes*. It is not, per se, an antimicrobial agent, as are some of the other topical $R_x$ antibiotics that are employed in the treatment of acne, e.g., clindamycin and erythromycin. The latter, of course, have no keratolytic effect, i.e., the ability to "dissolve" skin cells, breaking the thin skin barriers that cover the comedones, papules, pustules and nodules, and entrap the sebum, which lead to inflamed skin tissue.

The topical retinoid medicines, such as tretinoin, adapalene and tazarotene, are prescription drugs. They have desquamatory effects on the superficial skin layers, promoting drainage of the comedones, papules, etc., which characterize the disease. These topical retinoids may cause mild to moderate irritation in some patients. Although they have no direct antimicrobial activity, these $R_x$ drugs can exert some indirect activity by virtue of the fact that their actions render the follicular microclimate (biofilm) less hospitable to *P. acnes*.

The most common material used for the treatment of acne is salicylic acid. This material, a so-called β-hydroxy acid, has recognized keratolytic activity, as do many so-called α-hydroxy acids ("AHAs"; the α-prefix is a measure of the distance of the carbon-bearing hydroxyl group from the terminal carboxylic acid group.) Salicylic acid can "dissolve" skin tissue overlying the papules, pustules, etc., associated with the acne condition. In so doing, it promotes drainage of the blocked sebaceous glands and reduces the resulting inflammatory potential. Associated with the keratolytic activity of salicylic acid is a recognized skin irritancy. The FDA, in its "monograph" on accepted acne materials, allows salicylic acid to be used in acne medications at levels no greater than 2.0%. Obviously, the higher the level, the greater the potential for irritation. Alpha-hydroxy acids are also keratolytic, and to varying degrees have the ability to "dissolve" skin tissue, depending upon the nature of the acid. The most commonly used are glycolic acid and lactic acid. Others found in skincare products are malic acid, citric acid and tartaric acid and, the recent addition, mandelic acid. Because of concerns over the side effects of certain common α-hydroxy acids, in 1997, the FDA specified that the specific glycolic and lactic AHA concentrations in the product be 10% or less, its pH be 3.5 or higher, and it must have an effective sunscreen in the formulation or warn people to use sunscreen products.

Finally one additional $R_x$ product has been accepted by the FDA for treatment of acne, specifically azelaic acid. It is generally used to treat mild to moderate acne, as both a moderate antibacterial and an anti-inflammatory agent. Interestingly, it doesn't work well for acne that isn't infected with bacteria. Studies show that azelaic acid works as well as other topical $R_x$ formulations (containing such $R_x$ actives as benzoyl peroxide, tretinoin and antibiotics). But it has been reported to take one to two months after starting the application of topical azelaic acid compositions for the acne lesions to start disappearing.

It should be particularly noted that the materials cited above, for the treatment of acne, which are particularly effective, and with the exception of benzoyl peroxide, are all $R_x$ formulations. And even among those that are FDA approved, no component of any of the foregoing formulations is particularly noteworthy for its antimicrobial properties.

Relevant prior art known to the inventor, which addresses the foregoing prior art formulations and treatments, are Yu et al., U.S. Pat. No. 4,105,782, issued Aug. 8, 1978; Warshaw, U.S. Pat. No. 4,450,175, issued May 22, 1984; Song et al., U.S. Pat. No. 5,843,998, issued Dec. 1, 1998; Gross, U.S. Pat. No. 8,017,138 B2, issued Sep. 13, 2011; Bernstein, U.S. Patent Application Publication No. 2005/0084509 A1, issued Apr. 21, 2005; Peters, U.S. Patent Application Publication No. 2008/0311163 A1, issued Dec. 18, 2008; Cunliffe, William J., Acne, Martin Dunitz Ltd., London (1989); and, 21 C.F.R. Part 333, "Topical Acne Drug Products for Over-the-Counter Human Use," §333.310, disclosing acne active ingredients.

The composition of the present invention is a result of a search for a combination of agents which will provide the high-level antimicrobial activity lacking in the above commercial formulations, while also providing a keratolytic composition that is less irritating than the commercial compositions currently available. And if such a composition could be discovered, it could well have a positive impact on a host of other skin afflictions where microbial proliferation is a major problem. For example there are a number of bacterial skin infections and conditions, such as boils, folliculitis, carbuncles, furuncles, cellulitis, abscesses, impetigo, and erysipelas, where a powerful topical antibacterial composition could be decidedly beneficial. The same can apply to common fungal infections, including athlete's foot, jock itch, ringworm, and yeast infections.

SUMMARY OF THE INVENTION

It is, therefore, an object of the present invention to provide a multi-functional composition directed to the treatment of acne vulgaris (acne) and other skin afflictions.

It is a further object of the invention to provide multiple keratolytic and germicidal agents for use in such treatment.

It is, yet, a further object of the invention to provide compositions containing multiple keratolytic and germicidal agents, whereby at least one of the antimicrobial agents is created by combining two parts of the presently claimed composition, so that acidification of a nitrite salt in one part of the composition results in the formation of nitrous acid, which exhibits a great germicidal rapidity against a broad spectrum of bacteria and fungi.

It is an additional object of the present invention is to supplement the germicidal activity of the two-part system of the inventive composition through inclusion of mandelic acid, a known keratolytic acid, whose powerful germicidal activity, particularly against the *P. acnes* bacterium, has heretofore not been taught as part of a method for the treatment skin ailments, which combines keratolytic and germicidal properties.

It is a further object of the present invention is provide for the application of the inventive composition by a variety of methods, for example, either by initial mixing of individual precursor parts of the composition prior to application, or by individual ad seriatim application of each of the two parts, in either sequence, to accomplish specific treatment goals.

The foregoing and related objects are accomplished by the topical composition of the present invention, which is prepared by combining two individual precursor aqueous compositions (a term including gels and creams), the Acid (A) and Base (B) phases, by either of two methods:

a) directly prior to topical application of their mixture, or b) as an on-the-skin sequential application, by comingling the applied fluids following their individual sequential application to the subject's skin, either A→B, or B→A.

In the latter mode, the individual aqueous systems can be applied to the subject at an interval of up to 15-minutes between applications, such that each aqueous solution's components may react with the components of the other aqueous system, to create the panoply of active agents. The inventive composition, upon mixing in either manner, includes:

1) two keratolytic agents, i.e., the β-hydroxy salicylic acid and an α-hydroxy acid, wherein the latter, in a preferred embodiment, is mandelic acid. These acids are incorporated into the Acid (A) phase; and, 2) antimicrobial agents (Mandelic and Nitrous acids.)

a) Mandelic acid—Mandelic acid, in a preferred embodiment, in addition to its keratolytic property, possesses significant germicidal activity. With respect to antimicrobial activity as provided by the A phase components, per se, while salicylic acid is generally recognized as a mild antibacterial agent, mandelic acid is by far the most powerful of all the α-hydroxy acids. To put this into perspective, lactic acid has been shown to be a stronger antimicrobial acid than all the common α-hydroxy acids, with the exception of mandelic acid. The inventor has shown, in earlier studies, that while lactic acid surpasses the germicidally-effective α-hydroxy acid malic acid by killing 500-times more of the pathogenic organism *E. coli* within 30-seconds of contact, mandelic acid surprisingly kills 3000-times more of that organism than does even lactic acid under the same conditions. And with respect to malic acid, mandelic acid destroys 1.5 million times more *E. coli* cfu in that same time frame. Mandelic acid is structurally similar to lactic acid, except that the α-methyl group in lactic acid is replaced by a phenyl group in mandelic acid. The phenyl group makes mandelic acid more lipophilic, so that it is more attracted to the lipids in bacterial and fungal cell walls, as well as to the lipids of the skin, to which has a great affinity. The latter quality enhances both the germicidal and keratolytic efficacies of mandelic acid. Additional keratolytic α-hydroxy acids, such as lactic and glycolic acid, may be further used in the inventive composition. Their presence may also help buffer the pH of the Acid (A) phase.

b) Nitrous Acid. The Base (B) phase, of the inventive composition, includes a nitrite salt. This compound is the source of significant further germicidal activity of the mixed composition upon acidification by Phase A, whereby a major portion of the nitrite ion is transformed to nitrous acid. This is a remarkably effective antimicrobial material, which surpasses even that of mandelic acid, by a substantial margin. The highly-efficient nitrous acid antimicrobial is formed, to a fractional degree, from the acidification of the nitrite ion (in part B of the two-part composition) by $H^+$ ions generated by the partial ionization of both salicylic and mandelic acids in the phase A; and preferentially by even stronger $H^+$ ion donors, such as phosphoric, citric and/or hydrochloric acids. The latter may be included in Phase A of the composition, to spare consumption of $H^+$ ions from salicylic and the α-hydroxy acids, through acidic transformation of the nitrite salt to nitrous acid. The stronger acids may be included in that phase so that the pH of the mixed system is in a range to both optimize the efficacy of the salicylic and mandelic acids (higher keratolytic and/or antimicrobial activity balanced against skin irritancy potential), as well as to ensure that the nitrous acid that is formed in the mixed matrix is at a balanced (nitrous acid/nitrite) ratio to ensure the desired efficacy and stability of the nitrous acid. The equilibrium this refers to is shown in the following relationship, wherein the pH determines the balance:

$$Na^+NO_2^- \leftarrow \pm H^+ \rightarrow HONO + Na^+$$

The inventor has discovered that the nitrous acid system, when adjusted to a desired level of solution acidity, is capable of a remarkable degree of antimicrobial activity. The following table shows the correlation between pH and degree of conversion of nitrite ion to nitrous acid. The balance of the species will determine the germicidal capability of the system; the higher the pH the lower the activity but the greater the solution stability, and the lower the pH the greater the activity but the lower stability.

TABLE 1

Percentage of Nitrite as Nitrous Acid at Varying pH Values

| pH | Nitrous Acid % | Nitrite % |
|---|---|---|
| 1.5 | 98.4 | 1.6 |
| 2.0 | 95.2 | 4.8 |
| 2.3 | 90.9 | 9.1 |
| 2.6 | 83.3 | 16.7 |
| 2.8 | 76.0 | 24.0 |
| 3.0 | 66.7 | 33.3 |
| 3.3 | 50.0 | 50.0 |
| 3.5 | 38.8 | 61.2 |
| 4.0 | 16.6 | 83.4 |
| 4.5 | 6.0 | 94.0 |
| 5.0 | 2.0 | 98.0 |

Aqueous solutions of nitrous acid are unstable, and decompose according to the following equation. Instability increases with increased absolute and relative molar concentrations of the HONO, and with increasing heat:

$$3HNO_2(aq) \leftarrow \rightarrow H^+(aq) + 2NO(g) + NO_3^-(aq) + H_2O(l)$$

$$3HNO_2(aq) \leftarrow \rightarrow H^+(aq) + 2NO(g) + NO_3^-(aq) + H_2O(l) \quad \text{Equation 1}$$

The reaction is a combination of the two half-reactions, as follows:

$$2\{HNO_2 + H^+ e^- \leftarrow \rightarrow --- > NO + H_2O\} \quad \text{Equation 2}$$

$\epsilon° = 1.00$ volts $$HNO_2 + H_2O \leftarrow \rightarrow NO_3^- + 3H^+ + 2e^- - \quad \text{Equation 3}$$

$\epsilon° = -0.94$ volts $$\Sigma = 3HNO_2(aq) \leftarrow \rightarrow H^+(aq) + 2NO(g) + NO_3^-(aq) + H_2O(l)^-$$

In addition to the concentration-dependent degradation of nitrous acid, as shown above, nitrous acid will also act as an oxidizing agent in the presence of oxidizable materials, such as microorganisms, according to the first half-cell reaction above (Equation 2), with a redox potential $\epsilon° = 1.00$ volts. Accordingly, nitrous acid systems are quite destructive of all classes of microorganisms which are susceptible to oxidation, including bacteria, yeasts, molds and viruses. This destruction is well known for other non-specific oxidizing germicides such as bleach (hypochlorous acid), chlorous acid, chlorine dioxide, and iodine. Indeed microbiocidal data developed by an independent laboratory on a pre-mixed typical formula of the inventive composition show the outstanding capacity of a system comprised of nitrous, mandelic, and salicylic acids, which outperforms, by many orders of magnitude, the antimicrobial activity of well-regarded commercial acne treatment formulations. These data, and the formulation from which they were obtained, are provided in Example 1 of the instant disclosure.

It should be noted that the U.S. Food & Drug Administration allows the sale of over-the-counter acne drugs under 21 C.F.R. Part 333, "Topical Acne Drug Products for Over-the-Counter Human Use." Under 37 C.F.R. §333.310, Acne active ingredients: (a) lists salicylic acid 0.5 to 2 percent. Salicylic acid, by its very nature as a keratolytic agent, has an inherent skin irritancy, as do all the other α-hydroxy acids. In developing an effective acne composition, it is important therefore to establish a pH for the formulation that provides sufficient of the salicylic acid in its unionized form

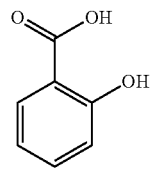

to dissolve the skin tissue. The ionized salicylate form

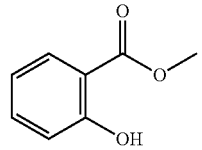

has no such activity. The pH for these inventive compositions is of great significance. A pH should be chosen for both the Part A alone and the Part B alone, as well as the pH of the resulting mix, such that they individually, and upon combination, are of optimum efficacy, stability, and of minimum irritation potential.

Part A Considerations:

The antimicrobial and the keratolytic activities of the three acid components (at least two (e.g., salicylic and mandelic acids) from Part A and the third formed upon combination of Parts A and B (i.e., nitrous acid)), either after pre-mixing or sequential mixing one the subject's skin, is significantly dependent on the relative amount of the free acid form of each of the particular compounds vis-á-vis its inactive salt form.

The $pK_a$ of salicylic acid is 2.97, which means that when salicylic acid is a component of an aqueous composition at a pH of about 3.0, one-half of that compound will exist in the active keratolytic acid form and one-half will be present in the inactive salt form. It is generally recommended that a salicylic acid-based acne treatment composition have a pH in the range of from about 3.0 to about 3.5. The lower the pH the greater the potential efficacy, but also the greater potential irritation. To put this into perspective, whereas at pH 3.0 there is a 50:50 ratio of active and inactive (acid:salt) forms, at a pH of about 3.5, the ratio of acid:salt forms drops to about 25:75. And at a pH of ~3.3, the ratio is about 33:67. The relative amounts will constitute part of the considerations when formulating compositions based on this inventive disclosure.

The same consideration of activity vs. acid:salt forms applies to mandelic acid, where the antimicrobial activity of an aqueous solution containing this material is strongly dependent on the pH of the system. Mandelic acid is inherently a weaker acid than salicylic acid, having a $pK_a$ of 3.41. Thus at pH levels common to commercial salicylic acid formulations, generally at pHs of about 3.0 to about 3.5, there will be a significant fraction of the mandelic acid available for germicidal activity, i.e., about 45% to about 70% as free acid, as seen shown below:

| Percentage of Mandelic Acid in Acid and Salt forms at Varying pH Values | | |
|---|---|---|
| pH | Mandelic Acid % | Mandelate % |
| 2.46 | 90 | 10 |
| 2.81 | 80 | 20 |
| 3.04 | 70 | 30 |
| 3.23 | 60 | 40 |
| 3.41 | 50 | 50 |
| 3.59 | 40 | 60 |
| 3.78 | 30 | 70 |
| 4.01 | 20 | 80 |

And of notable coincidence, the same pH range is optimum for the germicidal activity of nitrous acid, when the inventive compositions are adjusted to pH values from about 3.0 to about 3.5, upon combination of Parts A and B. This pH range applies to both the premixed A+B composition, or to the pH that obtains when the parts are applied sequentially to the skin, either Part A then Part B, or Part B then Part A. (The pH of the sequentially applied mixture on the skin is assumed to be that for the premixed A+B phases.) A section of the acid:salt form table, shown previously for nitrous acid as a function of pH, is provided below, to bracket pH ranges appropriate to the inventive compositions disclosed herein.

| Percentage of Nitrite as Nitrous Acid at Varying pH Values | | |
|---|---|---|
| pH | Nitrous Acid % | Nitrite % |
| 2.8 | 76.0 | 24.0 |
| 3.0 | 66.7 | 33.3 |
| 3.3 | 50.0 | 50.0 |
| 3.5 | 38.8 | 61.2 |
| 4.0 | 16.6 | 83.4 |

As is evident from this tabulation, by adjusting the pH of the inventive composition to a range, upon combination of Parts A and B, to about 3.0 to about 3.5, the nitrous acid generated upon their combination will represent from about 40% to almost 70% of the nitrite moiety in the free acid (germicidal) form. This has been determined to be an optimum range for the relative stability of the metastable nitrous acid that is formed (the species responsible for the high germicidal activity) which serendipitously overlaps both the active ranges of both mandelic and salicylic acids, in their respective roles as germicidal and germicidal+keratolytic agents, at acidities where skin irritation is considered to be of minimal concern. The inventor has seen, from earlier investigations of nitrous acid germicidal systems, that the longer-range stability of nitrous acid systems is significantly diminished when the HONO (nitrous acid) form of the nitrite system exists in ratios of >~2:1 acid/salt. The disproportionation of nitrous acid proceeds too rapidly, with a significant evolution of NO, and loss of desired germicidal reserve (see, Equation 1 above.) Contrary to common belief, the NO molecule is not highly germicidal, and it has been evident to this inventor that, even when all the NO of an activated nitrite system has been lost by evaporation and/or by reaction with oxygen to form the $N_2O_4$ molecule, the high germicidal action of acidified nitrite systems remains at equal, or even greater activity than the original mixture (as more $H^+$ is slowly generated [see Equation 3], creating more HONO than initially.)

As implied by the above, the desired pH range of from about pH 3 to about pH 3.5, for these inventive compositions, upon combination of both Parts A and B (premixed or sequentially applied), must be achieved by due consideration of the initial pH values of the individual Parts A and B, and such other factors as the buffering capacity of each part, and the relative volumes of each part when the two parts are combined. In general, the presence of the two α- and β-hydroxy acids, preferably mandelic and salicylic acids, which can function to buffer the pH of the A phase, will play a strong role in maintaining the pH of the combined system relatively close to the initial pH of part A, assuming the following:

The relative volumes of Parts A and B, in the intended use of the inventive composition, approximate 1:1. In certain circumstances, where the desired volume for one of the parts (more likely for Part B), the higher the relative volume of Part B the greater the tendency for an elevation of the pH of the combination (see detailed consideration of the Part B composition in the following section.)

The composition of Part B. There is little need for a pH much above pH 7.5-8.5, simply to ensure the stability of the nitrite salt. As will be seen, there are a number of optional materials that can be included in part B, to provide further benefit to the inventive composition in addition to it being a source of the powerful nitrous acid germicide, which forms upon combination with part A. A person skilled in the arts of chemistry and so-called cosmeceuticals will be familiar with those beneficial skin components that are stable in the mildly alkaline environment of part B.

It will be recognized that the acidity associated with a part A+B mixture, with a stipulated pH of about 3.0→3.5, refers to a $H^+$ concentration approaching 4 logs (10,000) below neutrality (pH=7.) Consider that a Part B formulation at, for example, pH=8, is one log (10) above neutrality, so even without considering any Part A buffering components, a Part A solution in the pH=3 range has 1,000-fold greater capacity to neutralize any alkaline source in Part B, with minimum impact on overall pH. Consistent with these considerations, I have determined that the various typifying Part B formulations shown in the following Examples have a relatively limited impact on the pH of the inventive, mixed compositions. As a result, the pH of the Part A formulation will generally be significantly different from the A+B mix pH, after due consideration of any dilutive effects by the Part B composition. Of course should other Part B components be found to be beneficial partners in this disclosed A+B inventive composition, wherein the Part A formulation has an initial pH significantly below that of the mixed composition, then a skillful practitioner would have little difficulty in making the appropriate adjustment to achieve the same stipulated mix pH range.

With respect to the levels of inclusion of both salicylic and the α-hydroxy acid in Part A where mandelic acid is the α-hydroxy acid in a preferred embodiment, the following considerations apply.

Regarding salicylic acid, its concentration, in the combined formulation, should lie in the range of from about 0.5% to about 5.0%. In the circumstance where the part A is applied to the skin prior to the application to part B, the concentration of salicylic acid in part A should not exceed 2.0%. This is consistent with the US FDAs monograph covering the sale of OTC acne drugs under 21C.F.R. Part 333 "Topical Acne Drug Products for Over-the-Counter Human Use." Under §333.310, Acne active ingredients. (a) is listed Salicylic acid 0.5 to 2 percent. When the alternate sequence of application is followed, namely part B then part A, the concentration of salicylic acid in the composition which forms upon their mixture on the skin, by physical means (such as finger tips or a cotton swab), should not exceed the stipulated 2.0%. Similar considerations apply with respect to the lower use level for salicylic acid, where adjustments are made in the selection of the designated 0.5% lower concentration limit contingent upon the sequence of application and, of course, the relative volumes of the two parts to be applied.

Regarding the α-hydroxy acid in Part A, excluding mandelic acid and its preferred embodiment: In general its concentration, in the combined formulation, should lie in the range of from about 0.5% to about 5.0%. When the inventive technology is for use in topical applications other than for acne vulgaris, a variety of α-hydroxy acids may be used, all of which have antimicrobial activity in addition to their recognized keratolytic properties. These include mandelic, glycolic, lactic, malic, citric, and tartaric acids. As discussed below, the inventive compositions, including any or many of these acids, have good efficacy in the treatment of a variety of skin conditions. For the treatment of acne vulgaris, an exception is made, requiring the avoidance of glycolic and lactic acids, in these compositions. And with the exception of those two acids, the stipulated pH range of the mixed formulation, irrespective of sequence of application or pre-mixed, should be about 3.0 to about 3.5. The U.S. Food & Drug Administration requires keratolytic products containing glycolic and/or lactic acids to have pH values≥pH 3.5. For emphasis of the foregoing, compositions of this inventive disclosure which are intended for use for skin afflictions other than for acne vulgaris, may be prepared where the pH range of the A+B combination can have the same pH in the 3.0→3.5 range. Practically speaking the use of lactic and/or glycolic acid in this disclosure for the treatment of acne vulgaris is contraindicated.

With specific reference to mandelic acid, as the sole or one of several α-hydroxy acids in Part A, in a preferred embodiment, its level of inclusion in Part A should be dictated by the desired level in the mixed combination of parts A and B, irrespective of whether Parts A and B are premixed, or applied to the subject's skin sequentially, in either the Part A then Part B, or the Part B then Part A order. The desired level of mandelic acid in that mixed combination should lie the in concentration range of from about 0.2% to about 5.0% range, in a preferred range of from about 0.5% to about 2.5%, and in a most preferred range of from about 0.75% to about 2.0% concentration. This applies to the use of the inventive composition for the topical treatment of both acne vulgaris and other skin afflictions.

As part of the foregoing disclosure, the primary focus was directed to the source of the additional strong germicidal activity provided by the nitrite salt, upon combination with the Acidic A phase. As further described herein, it is pointed out that a mild alkaline medium is all that is required for the nitrite salt to have an appropriate long-term stability. That generally should be in the pH range from about 7.0 to about 9.0. There is no reason that the upper limit cannot be extended to higher pHs, although this would then require an appropriate level of additional activating acid to reduce the nitrite to the general mix range of a pH of about 3.0 to about 3.5. That activating acid does not necessarily have to be either the salicylic or mandelic acid, in the preferred embodiment, and the requirement could readily be provided by, for example, a stronger mineral acid. The lower limit for stability of the nitrite salt could actually extend below pH 7.0, to about pH 6.5.

Other beneficial agents can be incorporated into phase B, where the term beneficial applies to qualities which impart both a) physical; and b) physiological qualities. In the former "a" category are included textural qualities, e.g., viscosity modifiers (see more detailed section below), surfactancy qualities e.g., non-ionic and anionic surfactants, appearance and coloration, pH adjustment and buffering e.g., sodium carbonate which forms sodium bicarbonate. In category "b" are included those materials which impart beneficial qualities to the skin e.g., allantoin and silicone-compounds providing smoothness. The selection and level of use of these materials are well known to those who are familiar with cosmetic formulation development.

With regard to the level of use of the nitrite salt, as represented by sodium nitrite in the following range specification, it has been found that appropriate levels of supplemental germicidal activity can be achieved (on the basis of a 1:1 volume use of Parts A and B) with levels of sodium nitrite in B from about 0.2% to about 5.0%, preferably in the range of about 0.4% to about 2.5%, and most preferably in the range of about 0.75% to about 1.5%. With other soluble nitrite salts, such as potassium nitrite, the weight ranges should be suitably adjusted. It should be again noted, that the intended ratio of Parts A and B, mixed prior to application or ad seriatim, must be taken into consideration in regard to both achieving the corresponding concentrations of the nitrite salt, and the desired mix pH of the inventive composition in the approximate pH range of from about 3.0 to about 3.5. With regard to the concentration ranges of the nitrite salt in Part B, their levels should be adjusted up or downwards, depending on the relative use ratios of the A/B combination. In general, the higher the relative amount of Part A, the higher the relative concentrations of the nitrite salts, in proportion to the use ratio of A and B parts. And the opposite situation applies if the ratios are reversed. With regard to pH, if the pH of the B phase in a particular formulation is, e.g., say, 8.5, and it is desired for example to first apply one part of A, on a random small set of acne blemishes on a subject's face, and thereafter apply a relatively larger three parts of B over the entire face, so as to deposit certain beneficial agents onto the skin, then the acidity and alkalinity of parts A and B, respectively, should be adjusted initially so that the mix pH of 1A:3B falls within the stipulated range of about pH 3.0→3.5. It should be obvious, to those who practice in the arts of cosmetic and cosmeceutical chemistry, that due consideration must be paid to the viscosity of each component, as discussed hereinafter, when determining the relative volumes of Parts A and B intended to be applied, in any of the ways described.

Other objects and features of the present invention will become apparent when considered in combination with the following detailed description of the invention, which provides certain preferred embodiments and examples of the present invention. It should, however, be noted that the accompanying detailed description is intended to discuss and explain only certain embodiments of the claimed invention and is not intended as a means for defining the limits and scope of the invention.

DETAILED DESCRIPTION OF ADDITIONAL PREFERRED EMBODIMENTS

In the application of this technology, it is often preferable to incorporate a thickening (gelling) agent to one or both parts of the two-part system, to add "body" to the composition. This allows for a greater deposition of the mixed material to skin surfaces, and a greater duration of action. Gelling agents for use in the present invention include polysaccharides extracted from legume seeds, such as the galactomannans, including guar gum and locust bean (carob) gum. Other gelling agents include high molecular weight polyoxyalkylene crosslinked acrylic polymers as well as the highly preferred cellulosics such as hydroxymethyl cellulose, hydroxypropyl cellulose, hydroxyethyl cellulose, methyl cellulose, methylpropyl cellulose, among others, including high molecular weight polyethylene glycols, polyacrylamide and polyacrylamide sulfonates, and crosslinked polyvinylpyrrolidones, among others.

As indicated in the title of this inventive composition, "Multifunctional Topical Formulation for the Treatment of Acne Vulgaris and Other Skin Conditions," there are a variety of other microbially-associated skin disorders which can benefit substantially from the application of compositions incorporating the inventive powerful topical antibacterial technology. These conditions, as referenced in Section 2. Description of the Related Art, include a host of other skin afflictions where microbial proliferation is a major problem. Examples in the category of bacterial skin infections and related conditions are boils, folliculitis, carbuncles, furuncles, cellulitis, abscesses, impetigo, and erysipelas. There is indeed a great need for an antimicrobial composition to treat diabetic foot ulcers, which result from deficient blood flow to peripheral tissues, such as in the feet of diabetes sufferers, where the necrotic tissue becomes a source of nutrients to invading bacteria. These often lead to foot amputation. There is the intriguing possibility, in such cases, that the nitrous oxide, NO, which is generated from nitrous acid degradation, as shown earlier in this Specification ($3HNO_2 \leftrightarrow H^+ 2NO + NO_3^- + H_2O$) can penetrate to the underlying capillaries and stimulate their dilation, leading to enhanced blood flow, thereby helping to counter the ischemia resulting from diminished oxygen supply to the affected tissues. Also of potential benefit from the inventive technology are those afflictions related to common fungal infections, including athlete's foot, jock itch, ringworm, and yeast infections.

The present invention is illustrated by the following Examples. All parts and percentages therein, as well as the Specification and claims, are by weight, unless otherwise specified. The following examples, which are non-limiting, further describe preferred embodiments within the scope of the present invention. Many variations of these Examples are possible without departing from the spirit of the invention.

Example 1

Example 1 demonstrates the antimicrobial activity of a formulation in which Parts A and B were mixed together immediately prior to their evaluation against the gram-positive aerotolerant, anaerobic bacterium *Propionibacterium acnes* (*P. acnes*) that is associated with acne. The formulas for Parts A and B of this inventive composition were as follows:

Part A:

| COMPONENT | Percentage |
| --- | --- |
| Isopropyl alcohol (70%) | 35.70 |
| Sodium benzoate | 0.04 |
| Salicylic acid | 1.00 |
| Mandelic acid | 1.00 |

| COMPONENT | Percentage |
| --- | --- |
| PLURONIC ® P103 (BASF Corporation) A difunctional block copolymer surfactant terminating in primary hydroxyl groups. A nonionic surfactant that is 100% active and relatively nontoxic. | 0.10 |
| Propylene glycol | 10.00 |
| NATROSOL ® 250MR (Ashland Specialty Chemical) (hydroxyethylcellulose) | 2.10 |
| Titanium dioxide (fine) | 0.10 |
| Deionized water | 49.96 | pH adjusted to ~2.8 with conc. NaOH

Part B:

| COMPONENT | Percentage |
| --- | --- |
| PLURONIC ® P103 (BASF Corporation) A difunctional block copolymer surfactant terminating in primary hydroxyl groups. A nonionic surfactant that is 100% active and relatively nontoxic. | 0.1 |
| Dodecylbenzene sulfonate, Na$^+$ | 0.1 |
| Sodium Nitrite (pure basis) | 1.0 |
| NaOH (10N) | ~2.2 |
| Carbopol ® 980 (polymer is a crosslinked polyacrylate polymer) | 1.0 |
| Titanium dioxide (fine) | 0.1 |
| Deionized Water | ~95.5 | pH adjusted to ~8.5 -- The pH of the mixed composition was 3.25

The microbiological results from testing this freshly mixed composition on the *P. acnes* bacterium, were as follows:

Test Organism: *P. acnes* ATCC 6919
Initial Suspension: $2.3 \times 10^7$

| Test Sample | Challenge Inoculum (Log#cfu/ml) | Recovered (Log#cfu/ml) | Log Reduction |
| --- | --- | --- | --- |
| Inventive Composition rdk110PGX235 A + B | $2.3 \times 10^6$ (6.36) | 0 (0) | >>5.36 |
| Acne Free ™ Terminator 10 | $2.3 \times 10^6$ (6.36) | >1 × 10$^{4*}$ (>>4.0) | <<2.5 |
| Proactiv Solution ® (Rodan and Fields) | $2.3 \times 10^6$ (6.36) | >1 × 10$^{4*}$ (>>4.0) | <<2.5 |
| Control (Saline) | $2.3 \times 10^6$ (6.36) | $2.3 \times 10^6$ | |

*Approximate Minimum Count

It can be noted, from the Log Reduction data, that the efficacy of a specific formulation of the inventive composition is at least 1,000 times (>3 logs) greater than any of these commercial products, and particularly that approximately 6 logs (1 million) of organisms, per ml of test medium, were destroyed within one minute of contact with this representative formulation of the inventive composition. The other two commercial formulations, each of which contain 2% of salicylic acid as cf. the 0.5% salicylic acid in the mixed composition, showed no significant reduction of the *P. acnes* organism count, after the 60-second contact. This is not unexpected because the primary focus of these two commercial products was on the acne pustules, papules, etc., rather than the microorganism that is invariably present on the skin of acne patients, as a probable exacerbant of their skin affliction.

Example 2

Example 2 illustrates the efficacy of the formulation shown in Example 1 in the treatment of acne-afflicted subjects. It was a "prospective, comparative, randomized clinical study" involving twenty-three female and twenty-one male individuals, aged 9-29; twenty-two of whom had lesions on their faces, chests and backs; twelve on their faces only; and ten on their faces and backs. The patients were randomly divided in two groups, as follows:

Control: Conventional treatment with systemic antibiotics and topical retinoids;

Experimental: Topical treatment of the lesions with the premixed test formulation, twice a day for up to 4 weeks, with photos taken every week.

The following summary of findings was provided by the clinician who coordinated the study:
- The new treatment had the same efficacy as the conventional treatment
- The advantage is that the new treatment is potentially safer
- Conventional treatment is based on systemic antibiotics given for long periods and retinoids. Long term antibiotics can disrupt endogenous normal flora, and retinoids have been associated with hypertriglyceridemia and a high risk of suicide in adolescents

Example 3

Example 3 illustrates the efficacy of the formulation shown in the treatment of acne-afflicted subjects, when the Part A component is first only applied to the individual acne blemishes, and then the Part B application follows shortly thereafter, uniformly spread over the whole skin area where the acne is evident. The application of the Part A component is done by fingertip to the individual spots, while the Part B application is accomplished with a cotton swab. The Part A formulation has a higher viscosity, by virtue of inclusion of a NATROSOL® (hydroxyethylcellulose) thickener in its composition. Part B, which is activated to form nitrous acid primarily at the site of the acne infections, has a lotion-promoting component (Sepigel) which is often found in such types of formulations. The Part B also contains Allantoin (a chemical compound with formula $C_4H_6N_4O_3$; also known as 5-ureidohydantoin or glyoxyldiureide), which is recognized by cosmeceutical chemists to stimulate healthy, normal tissue formation. It has been classified by the FDA as an over-the-counter, Category I (safe and effective) active ingredient skin protectant.

Part A:

| COMPONENT | Percentage |
| --- | --- |
| Isopropyl alcohol (70%) | 35.70 |
| Sodium benzoate | 0.04 |
| Salicylic acid | 1.00 |
| Mandelic acid | 1.00 |
| PLURONIC ® P103 (BASF Corporation) A difunctional block copolymer surfactant terminating in primary hydroxyl groups. A nonionic surfactant that is 100% active and relatively nontoxic. | 0.10 |
| Propylene glycol | 10.00 |

-continued

| COMPONENT | Percentage |
| --- | --- |
| Natrosol 250HHR (hydroxyethylcellulose) | 1.30 |
| Blue #1 0.1% solution | 0.05 |
| Deionized water | 50.290 |
| Sodium Hydroxide 20% soln | 0.52 | pH of part A formulation was 3.42

Part B:

| COMPONENT | Percentage |
| --- | --- |
| PLURONIC ® P103 (BASF Corporation) A difunctional block copolymer surfactant terminating in primary hydroxyl groups. A nonionic surfactant that is 100% active and relatively nontoxic. | 0.10 |
| Dodecylbenzene sulfonate, Na$^+$ | 0.10 |
| Sodium Nitrite (pure basis) | 1.00 |
| NaOH (20% solution) | 0.05 |
| Sepigel 305 | 0.25 |
| Allantoin | 0.10 |
| Xanthan Gum | 0.10 |
| Deionized Water | 98.30 | pH adjusted to ~8.5

A number of young men and women, who had acne outbreaks on their skin, had applied this inventive composition ad seriatim, where the Part A was allowed to remain for a few minutes prior to smoothing on the Part B, as described above. They all reported that the individual acne blemishes had cleared within several days of application of this composition on a 2x/day basis.

Example 4

Example 4 illustrates the efficacy of the formulation shown in Example 1 in the treatment of non-acne skin conditions. Within several days of twice per day application of the mixed formulation, one individual with intractable folliculitis reported a remarkable reduction of the inflamed area, which theretofore was resistant to a variety of other medications. A young woman with widespread acne covering her upper torso and face, to a degree that she avoided appearing in public areas, had applied the composition twice a week to the affected areas. After one month the condition had completely disappeared. She also had suffered from *pityriasis alba*, which also was no longer evident one month after the twice-per-week application.

While only several embodiments of the present invention have been shown and described, it will be obvious to those skilled in the art that many modifications may be made to the present invention without departing from the spirit and scope thereof.

What is claimed is:

1. A method for treating acne vulgaris, comprising the steps of:
   formulating an acidic aqueous solution having salicylic acid and an α-hydroxy acid, with said acidic aqueous solution having no lactic acid and no glycolic acid;
   formulating an alkaline aqueous solution having an alkaline nitrite salt; and,
   sequentially applying said alkaline aqueous solution directly to the portion of the skin of the patient and three minutes to fifteen minutes later applying said acidic aqueous solution directly to the portion of the skin of the patient to which said alkaline aqueous solution has already been applied thereby producing nitrous acid, the activity of which supplements that of said acidic aqueous solution for treating acne vulgaris afflicting the portion of the skin of the patient, wherein the α-hydroxy acid concentration is in the range of from about 0.5% to about 5.0% as calculated based on a 1:1 combined volume of said acidic aqueous solution and said alkaline solution.

2. The method for treating acne vulgaris according to claim 1, wherein said acidic aqueous solution includes an α-hydroxy acid selected from the group consisting of malic acid, mandelic acid and a combination thereof.

3. The method for treating acne vulgaris according to claim 1, wherein said alkaline aqueous solution includes sodium nitrite as said alkaline nitrite salt of said alkaline part.

4. A method for treating acne vulgaris, comprising the steps of:

formulating an acidic aqueous solution having salicylic acid and mandelic acid, said mandelic acid being an α-hydroxy acid with said acidic aqueous solution having no lactic acid and no glycolic acid;

formulating an alkaline aqueous solution having an alkaline nitrite salt; and, sequentially applying said alkaline aqueous solution directly to the portion of the skin of the patient and three minutes to fifteen minutes later applying said acidic aqueous solution directly to the portion of the skin of the patient to which said alkaline aqueous solution has already been applied thereby producing nitrous acid, the activity of which supplements that of said acidic aqueous solution for treating acne vulgaris afflicting the portion of the skin of the patient.

5. The method for treating acne vulgaris according to claim 4, wherein said acidic aqueous solution further includes an additional α-hydroxy acid.

6. The method for treating acne vulgaris according to claim 5, wherein said additional α-hydroxy acid is malic acid.

7. The method for treating acne vulgaris according to claim 4, wherein said alkaline aqueous solution includes said alkaline nitrite salt of said alkaline part is sodium nitrite.

* * * * *